United States Patent [19]

Aebi et al.

[11] Patent Number: 5,047,029
[45] Date of Patent: Sep. 10, 1991

[54] CLAMP AND SYSTEM FOR INTERNAL FIXATION

[75] Inventors: Max Aebi, Bern; Robert Mathys, Jr., Bettlach, both of Switzerland

[73] Assignee: Synthes (U.S.A.), Paoli, Pa.

[21] Appl. No.: 333,307

[22] Filed: Apr. 5, 1989

[30] Foreign Application Priority Data

Jun. 10, 1988 [CH] Switzerland ..................... 2233/88

[51] Int. Cl.⁵ .............................................. A61B 17/58
[52] U.S. Cl. ..................................... 606/61; 606/59
[58] Field of Search ............ 128/69, 83, 92 Z, 92 ZY, 128/92 ZK, 92 ZW, 92 YM; 403/55, 82, 83, 84, 90, 91, 371, 370, 367, 368; 606/59-61, 72, 73

[56] References Cited

U.S. PATENT DOCUMENTS

| | | | |
|---|---|---|---|
| 1,578,634 | 3/1926 | Borgmann | 403/82 |
| 2,346,346 | 4/1944 | Anderson | 403/90 X |
| 2,391,693 | 12/1945 | Ettinger | 128/92 X |
| 3,568,963 | 3/1971 | Koskinen | 403/90 X |
| 4,271,832 | 6/1981 | Evans et al. | 128/92 ZW |
| 4,620,533 | 11/1986 | Mears | 128/92 R X |
| 4,673,376 | 6/1987 | Fender | 463/90 X |
| 4,693,240 | 9/1987 | Evans | 128/92 Z |
| 4,920,959 | 5/1990 | Witzel et al. | 606/53 |

FOREIGN PATENT DOCUMENTS

| | | | |
|---|---|---|---|
| 242708 | 10/1987 | European Pat. Off. | 128/92 Z |
| 2843711 | 4/1980 | Fed. Rep. of Germany . | |
| 3132520 | 6/1982 | Fed. Rep. of Germany . | |
| 3515678 | 11/1986 | Fed. Rep. of Germany . | |
| 8703022 | 4/1987 | Fed. Rep. of Germany . | |
| 2405063 | 5/1979 | France . | |
| 2531332 | 2/1984 | France | 128/92 ZW |
| 2557933 | 7/1985 | France . | |
| 2615095 | 11/1988 | France | 128/69 |
| 6639264 | 11/1983 | Switzerland . | |
| 2178323 | 2/1987 | United Kingdom . | |

OTHER PUBLICATIONS

Bulletin No. 70, Robert Mathys Co., Synthes, 4/1986.

Primary Examiner—Robert A. Hafer
Assistant Examiner—Kevin G. Rooney
Attorney, Agent, or Firm—Davis Hoxie Faithfull & Hapgood

[57] ABSTRACT

A coupling element for holding a Schanz screw and a threaded pin rigidly in the correct orientation comprising a jacket, an eye with a collet therein and a nut.

11 Claims, 3 Drawing Sheets 5,047,029

CLAMP AND SYSTEM FOR INTERNAL FIXATION

FIELD OF THE INVENTION

The present invention relates to a clamp or coupling for use in osteosynthesis to anchor vertebrae in the spinal column, and to a system using such clamp.

BACKGROUND OF THE INVENTION

Internal fixation devices or fixators which serve to rigidly couple a vertebra in the spinal column to one or more other vertebrae are known. In general they involve screws such as the so-called "Schanz" screws which are inserted into vertebrae and extend out more or less normally to the back of the patient, support rods which extend roughly parallel to the spine, and clamps or couplings which connect the screws with the support rod. Such fixators are described, for example, in the Synthes Bulletin of the Association for the Study of Internal Fixation, No. 70, dated March, 1986.

In systems according to the bulletin referred to, which are described more fully below, the Schanz screws are held by a kind of hook which presses the shaft of the screw against a clamp housing under the pressure of a nut turning on a screw on which the hook is mounted. This structure is difficult to work with. Moreover, the Schanz screw is not retained as rigidly as might be desired.

SUMMARY OF THE INVENTION

In accordance with the invention, there is provided a clamp or coupling device by means of which a screw such as a Schanz screw may be coupled to a support rod more rigidly than with prior devices. Moreover the structure according to the invention is much easier to manipulate and adjust.

A clamp or coupling according to the invention comprises a housing having a sleeve for receiving a support rod, an eye in said housing, a collet adapted to receive the shaft of a Schanz type screw, said collet having a compressible head and means for drawing said collet into said eye, the walls of said eye being conically shaped to compress the head of said collet as it is drawn into the eye, thereby to hold said screw in a desired orientation with respect to the support rod.

The invention further comprises fixation systems comprising a support rod, a plurality of clamps as described and a plurality of Schanz type screws.

THE DRAWINGS

The invention will be further described with reference to the accompanying drawings in which:

FIG. 2A is an exploded view of a prior art coupling.

DETAILED DESCRIPTION OF THE INVENTION

Figure 1:
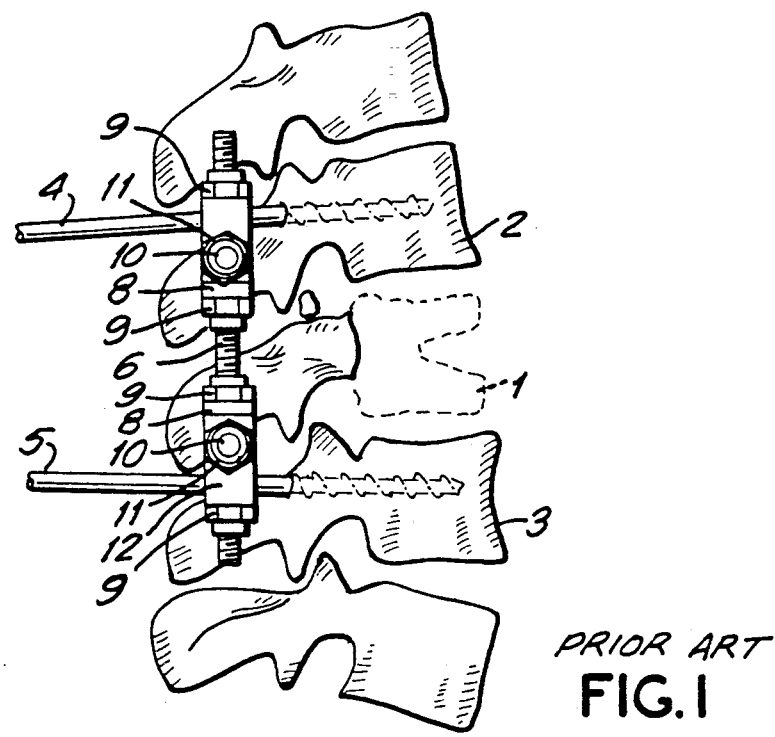
FIG. 1 is a schematic side elevational view showing a Schanz screw, a support rod and coupling devices known to the prior art applied to a segment of a spine.
Figure 2:
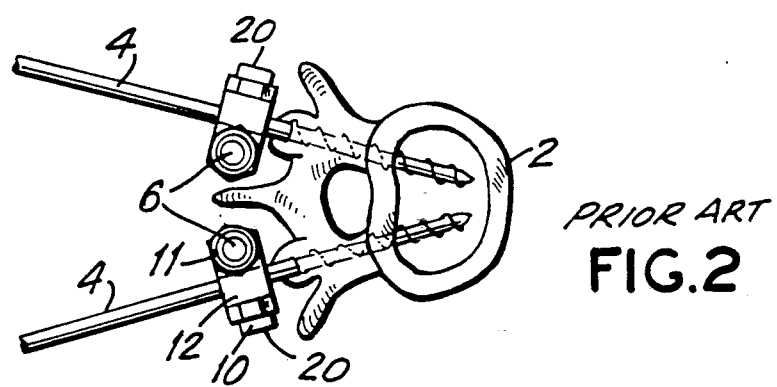
FIG. 2 is a plan view showing two sets of Schanz screws with coupling devices according to the prior art.

FIGS. 1 and 2 show the manner in which a coupling of the general type here concerned but employing coupling units according to the prior art, is used. In FIGS. 1 and 2, two Schanz screws 4 and 5 are inserted into each of two vertebrae 2 and 3 adjacent to a damaged vertebra 1 for rigid connection of the two sound vertebrae. Each Schanz screw 4 of upper vertebra 2 is rigidly connected via a threaded support rod 6 to the corresponding Schanz screw 5 of lower vertebra 3. The rigidity of the connection between each Schanz screw and support rod 6 is maintained by the clamps or couplings 20.

Details of the prior art couplings 20 are shown in FIG. 2A. Each coupling element has a block 7 which slides freely along support rod 6 and may be fixed at any position on the rod by means of nuts 9, threaded on rod 6, and retainer rings 8. Rings 8 have interior flats 25 which engage flats 26 on the rod 6. Rings 25 are free to slide along the rod 6, and are provided with a toothed or knurled section 27 which engages a like section 28 on the face of block 7. Thus when nuts 9 are tightened, engaging retainer ring 8 with the knurled section 27 of block 7, the block is fixed against rotation on the rod.

Block 7 has a threaded side extension 10 adapted to receive a ring hook 12. The ring part 31 of ring hook 12 has a knurled or toothed portion 32 adapted to engage a like portion 33 on the block 7. When fitted over side extension 10 and fixed by nut 11, the ring hook is thus prevented from rotating.

The hook portion 35 of ring hook 12 extends over the block 7, forming with the block an aperture in which a Schanz screw can be retained, the pressure exerted by nut 11 serving to prevent the pin from shifting or rotating.

This method of clamping Schanz screws has two disadvantages. First, it is difficult to gain access to the nut 11 with a small wrench. Second, not much tension can be transferred through the nut to the clamp jaw. This tension is further reduced because the stress produced by the tightening of the clamp jaw causes plastic deformation.

The clamp in the coupling element of the invention does not have these disadvantages.

Referring to FIGS. 3-6, a coupling unit 36 according to the invention comprises a housing 17, having a cylindrical sleeve 37, which enables the housing 17 to slide and rotate on a threaded support rod 6, identical with the support rods shown in FIGS. 1-2. The housing also has an eye 13 with a conically shaped opening 13a. A tubular collet 14 is provided for receiving a Schanz screw 4 identical to the Schanz scraews shown in FIGS. 1-2. The collet 14 has a spherical compressible head 38, composed of a plurality of curved spring leaves 38a, at one end, and a threaded shaft 14a at the other. Flats 14b are provided on each side of the shaft 14a.

The collet 14 seats in the conical opening 13(a) of eye 13, the shaft of the collet extending through the eye and beyond the housing 7. Flats 41 are provided at the narrower end of opening 13(a). These flats engage the flats 14b on the shaft 14a of the collet 14 and prevent the collet from rotating when it is inserted in the eye.

The collet 14 is secured in the eye 13 by means of a retaining ring 16, which slides on shaft 14a and is provided with flats 42 to match the flats 14b on shaft 14a. A nut 15 engages with the threads on shaft 14a.

Figure 3:
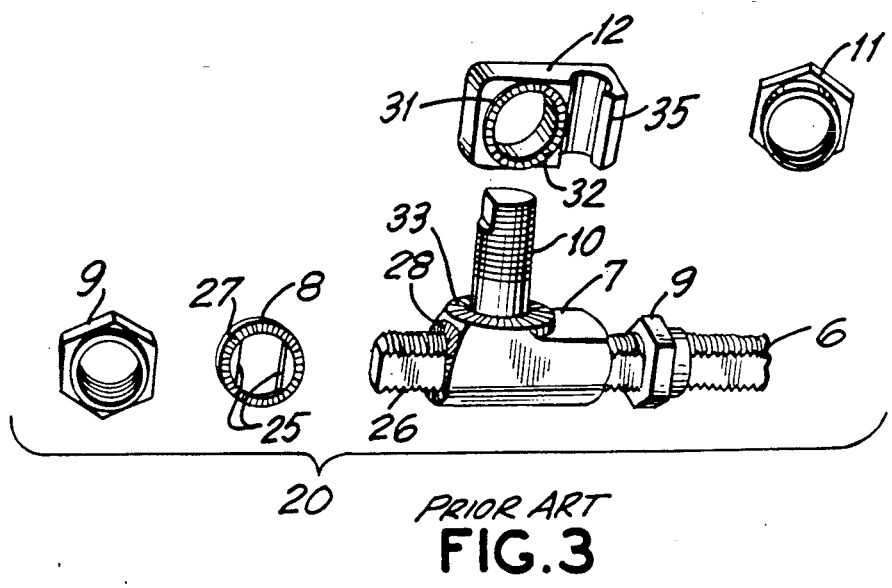
FIG. 3 is a schematic exploded view showing the several elements of a coupling device according to the invention in their relationship to one another and also to a support rod and a Schanz screw.
Figure 3:
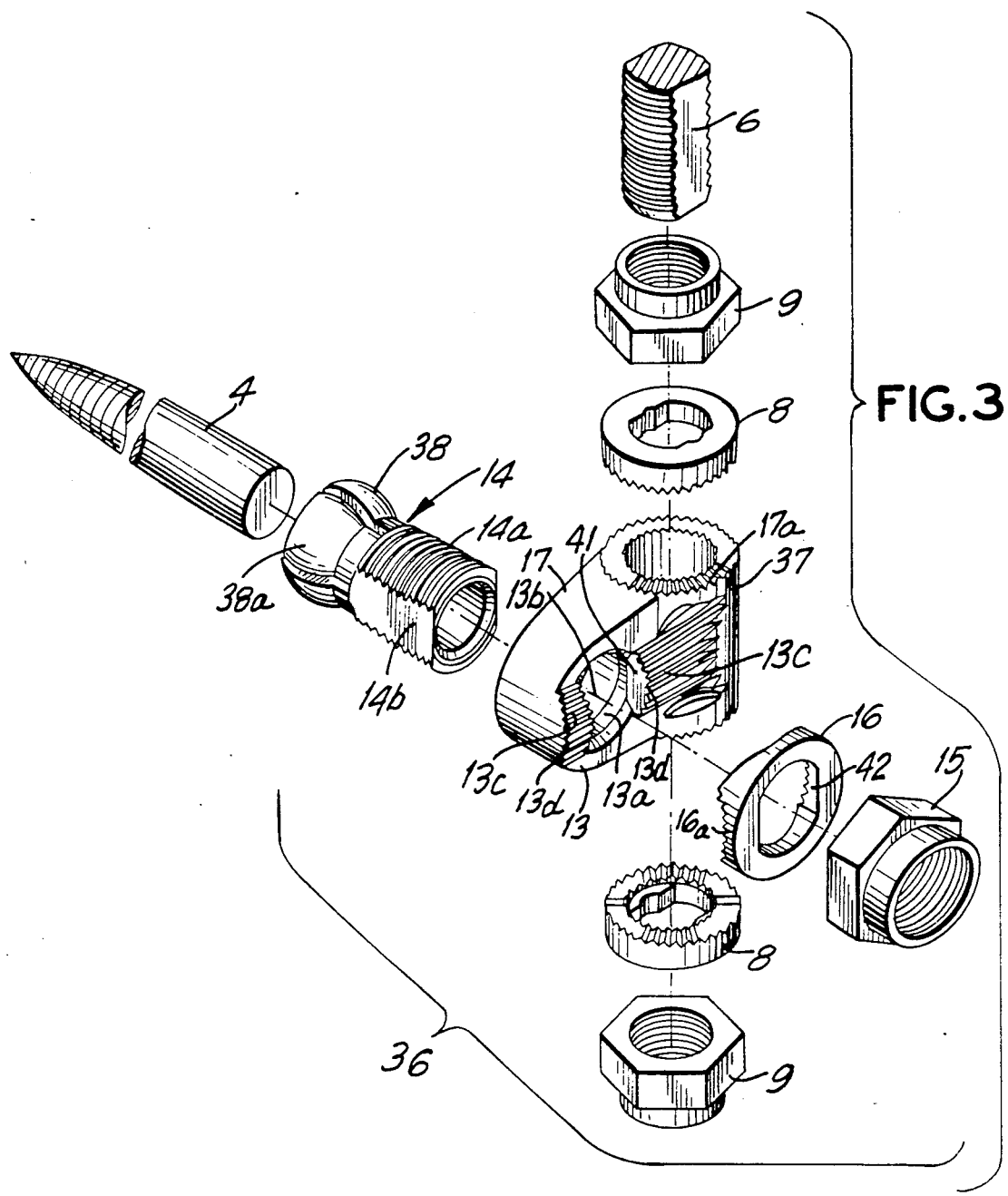
Figure 3A:
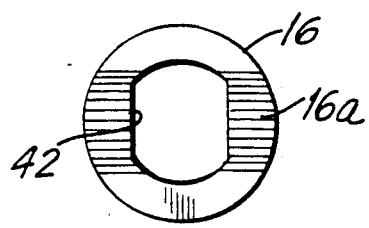
FIG. 3A is a front view of a retainer ring in the coupling unit of FIG. 3.
Figures 4, 6:
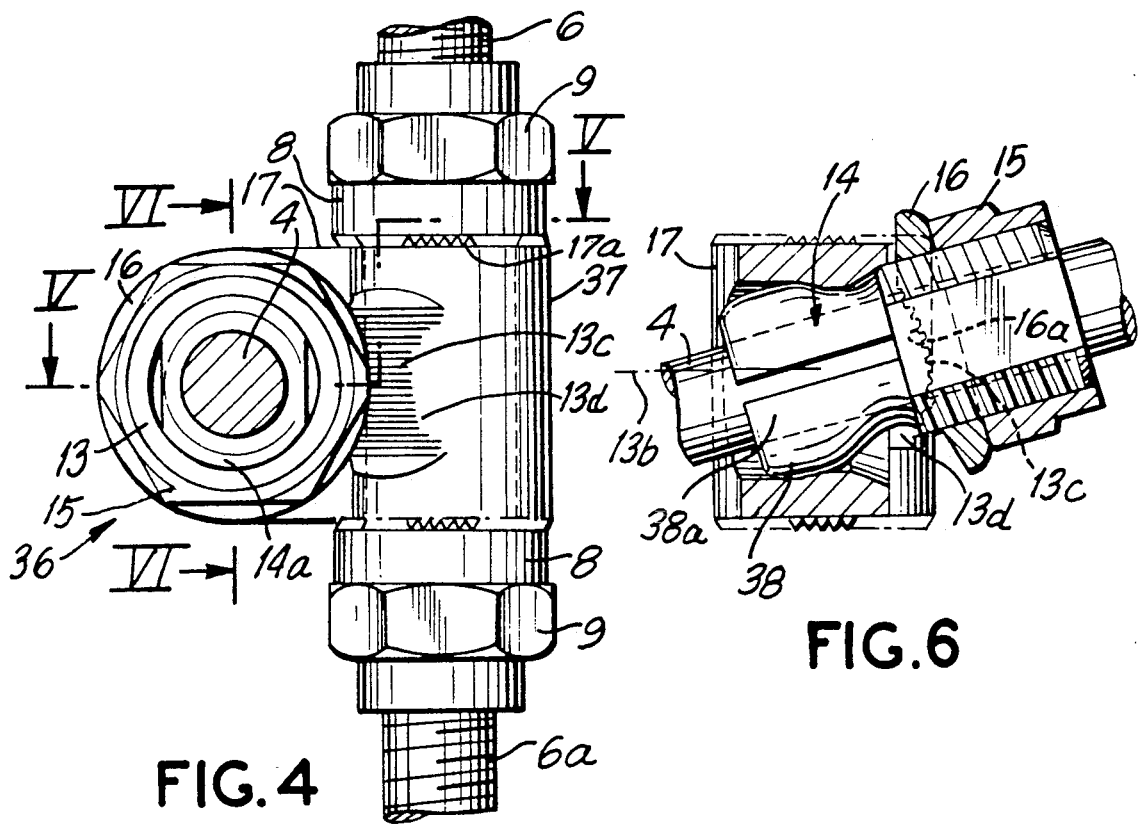
FIG. 4 is a front elevational view of a coupling unit according to the invention attached to a support rod and Schanz type screw.
FIG. 6 is a side view partly in vertical section of that portion of a coupling unit according to the invention designed to receive a Schanz type screw, with screw inserted.
Figure 5:
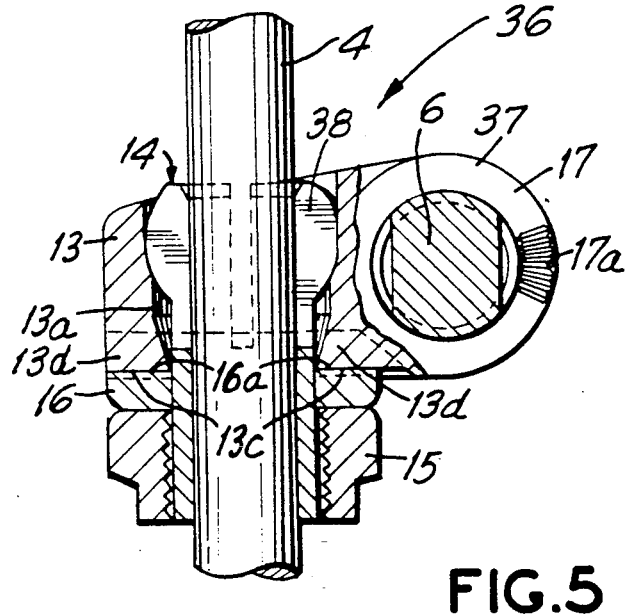
FIG. 5 is a top view, partly in horizontal section of the coupling unit of FIG. 4.

It is necessary for Schanz screw 4 to be able to tilt during the surgical operation and also for it to be able to be fixed in a position in which it is at an angle to the axis (shown as 13(b) in FIG. 6) of the conical opening 13(a). The compressible head 38 of the collet, as noted above, is spherical in shape (somewhat truncated) enabling it to be seated in the conical opening 13(a) with the ability to tilt in a vertical plane (as shown in FIG. 3), engagement of the flats 14b on the shaft of the collet with the flats 41 preventing tilting in the horizontal plane (as shown in FIG. 3). In order to maintain the desired position when tension is applied to the collet (i.e., when nut 15 is tightened), retainer ring 16 has two curved recessed areas, both of which are provided with teeth 16a. These teeth 16a mesh with teeth 13c which are provided on two side arches 13d at the edges of eye 13.

In use, a Schanz screw or the equivalent is inserted in collet 14, the screw is tilted to the proper angle and the nut 15 is turned down on shaft 14a. The teeth 16a on retainer ring 16 are thus brought into engagement with teeth 13c on the sides of the opening 13a. The compressible collet head 38 is drawn down into the conical opening 13a, compressing it about the Schanz screw and thus developing a firm grip on the screw.

The coupling may be moved up and down and rotated about the threaded rod 6 in the manner described above in connection with FIGS. 1, 2 and 2A. It may be set at any desired position and orientation by means of nuts 9 and retaining rings 8, which may have the same structures as those used in the prior art (FIGS. 1, 2 and 2A), teeth 17a engaging with the teeth on ring 8.

Due to its novel design, the coupling unit of the invention does not have the disadvantages of the prior art coupling noted above. The collet is significantly more effective than the prior art hook clamp. Furthermore, once the nut used for positioning the collet is applied using a socket wrench, its axis is in the surgeon's line of sight and the nut can be turned much more easily than a nut visible only from the side.

What is claimed is:

1. A coupling for use in osteosynthesis to connect a Schanz type screw with a support rod, said coupling comprising a housing having a sleeve for receiving a support rod, an eye in said housing, a tubular collet adapted to receive the shaft of a Schanz type screw, said collet having a compressible head, an axis means for axially drawing said collet into said eye, said eye having conically shaped interior walls to compress the head of the collet as it is drawn into the eye, thereby to hold said screw in a desired orientation with respect to said support rod and means for preventing rotation of said collet about its axis as it is drawn into the eye.

2. A coupling for use in osteosynthesis to connect a Schanz type screw with a support rod, said coupling compressing a housing having a cylindrical sleeve for receiving a support rod and clamp means for receiving and retaining a Schanz type screw, said clamp means comprising:
   a conically shaped eye in said housing having an axis transverse to the axis of said sleeve
   a compressible tubular collet, positioned in said housing and adapted to receive a Schanz type screw,
   means for drawing said collet axially into said eye to compress said collet and thus to cause said collet to grasp said Schanz type screw, and
   means for preventing rotation of said collet about the axis as it is drawn into the eye.

3. The coupling claimed in claim 2 wherein the collet has a spherical compressible head and a threaded shaft and comprising a nut on said shaft to draw said collet into said housing.

4. The coupling claimed in claim 3 wherein the collet has a shaft extending from said head, said shaft having external threads and a flat on at least one side.

5. The coupling claimed in claim 4 and comprising a flat on said housing adjacent the narrow end of the conical interior of said eye to engage the flat on the shaft of said collet.

6. The coupling claimed in claim 4 and comprising a retaining ring adapted to fit over the shaft of said collet, said ring having a flat to engage the flat of said collet shaft.

7. The coupling claimed in claim 4 or claim 6 and comprising a nut to engage the threads on said shaft and draw the collet into the eye of said housing.

8. The coupling claimed in claim 7 wherein the retaining ring has a knurled section and comprising a knurled area on said housing adjacent the opening of said eye for engaging the knurled section on said ring.

9. An internal fixation system for use in spinal osteosynthesis comprising a support rod, a Schanz type screw and a coupling for connecting the rod to the screw, said coupling comprising a housing, a sleeve in said housing for receiving said support rod and an eye in said housing for receiving the Schanz type screw, said eye having a central axis transverse to the axis of said sleeve, and a conically shaped opening, a collet having a compressible head and a shaft, means for drawing said collet axially into said eye to compress the head of the collet against the screw to grasp the screw and means for preventing rotation of said collet about the axis as it is drawn into the eye.

10. The system claimed in claim 9 and comprising means for fixing said housing to said support rod.

11. The system claimed in claim 9 and comprising means for fixing said collet in said opening at an angle to the axis of the eye.

* * * * *